United States Patent [19]
Riese et al.

[11] Patent Number: 5,944,104
[45] Date of Patent: *Aug. 31, 1999

[54] CHEMICALLY INDUCED STIMULATION OF SUBTERRANEAN CARBONACEOUS FORMATIONS WITH GASEOUS OXIDANTS

[75] Inventors: Walter C. Riese, Katy; Stephen V. Bross, Sugar Land, both of Tex.

[73] Assignee: Vastar Resources, Inc., Houston, Tex.

[*] Notice: This patent is subject to a terminal disclaimer.

[21] Appl. No.: 08/951,719

[22] Filed: Oct. 16, 1997

Related U.S. Application Data

[63] Continuation-in-part of application No. 08/846,994, Apr. 30, 1997, Pat. No. 5,865,248, which is a continuation-in-part of application No. 08/594,725, Jan. 31, 1996, Pat. No. 5,669,444.

[51] Int. Cl.$^6$ .............................. E21B 43/17; E21B 43/25; E21B 43/26; E21B 43/30
[52] U.S. Cl. ......................... 166/263; 166/245; 166/271; 166/305.1
[58] Field of Search .................................... 166/245, 263, 166/268, 401, 305.1, 308; 299/12, 16

[56] References Cited

U.S. PATENT DOCUMENTS

| | | | |
|---|---|---|---|
| 4,032,193 | 6/1977 | Drinkard et al. | 299/4 |
| 4,043,395 | 8/1977 | Every et al. | 166/268 X |
| 4,245,699 | 1/1981 | Steeman | 166/271 |
| 4,305,464 | 12/1981 | Masszi | 166/370 |
| 4,368,922 | 1/1983 | Hemphill et al. | 166/307 X |
| 4,391,327 | 7/1983 | De Carlo | 166/307 |
| 4,424,863 | 1/1984 | White | 166/268 |
| 4,537,252 | 8/1985 | Puri | 166/272 |
| 4,662,439 | 5/1987 | Puri et al. | 166/272 |
| 4,662,443 | 5/1987 | Puri et al. | 166/261 |
| 4,747,642 | 5/1988 | Gash et al. | 166/256 |
| 4,756,367 | 7/1988 | Puri et al. | 166/263 |
| 4,762,543 | 8/1988 | Pantermuuehl et al. | 62/28 |
| 4,765,407 | 8/1988 | Yuvancic | 166/268 |
| 4,833,170 | 5/1989 | Agee | 518/703 |

(List continued on next page.)

FOREIGN PATENT DOCUMENTS

| | | |
|---|---|---|
| 0181211 | 5/1986 | European Pat. Off. . |
| 1492238 | 11/1977 | Russian Federation . |
| 1492238 | 11/1977 | United Kingdom . |

OTHER PUBLICATIONS

Low temperature oxidation of brown coal. 3. Reaction with molecular oxygen at temperature close to ambient by Philip D. Swann and David G. Evans, Unviersity of Melbourne, Parkville Victoria, 3052, Australia, FUEL vol. 58, Apr. pp. 276–280.

X–ray Studies of Coal Oxidation by Herbert Beall, Bradley J. Howard, John T. Vaughey, Worcester Polytechnic Institute in ENERGY 7 FUELS 1988, 2, 721–722.

(List continued on next page.)

*Primary Examiner*—George Suchfield
*Attorney, Agent, or Firm*—F. Lindsey Scott

[57] ABSTRACT

A method for increasing the methane recovery from a subterranean carbonaceous formation by chemically stimulating the formation of cleats and increasing the surface area in the carbonaceous formation by injecting a gaseous oxidant into the carbonaceous formation to stimulate the formation of cleats in and increase the surface area of carbonaceous material in the carbonaceous formation; and thereafter producing methane from the carbonaceous formation at an increased rate. The gaseous oxidant may be ozone, oxygen or combinations thereof.

20 Claims, 3 Drawing Sheets

U.S. PATENT DOCUMENTS

| | | | |
|---|---|---|---|
| 4,883,122 | 11/1989 | Puri et al. | 166/263 |
| 4,913,237 | 4/1990 | Kutas | 166/308 |
| 4,973,453 | 11/1990 | Agee | 422/190 |
| 4,993,491 | 2/1991 | Palmer et al. | 166/280 |
| 5,014,785 | 5/1991 | Puri et al. | 166/263 |
| 5,014,788 | 5/1991 | Puri et al. | 166/280 |
| 5,048,328 | 9/1991 | Puri | 73/153 |
| 5,085,274 | 2/1992 | Puri et al. | 166/252 |
| 5,099,921 | 3/1992 | Puri et al. | 166/266 |
| 5,133,406 | 7/1992 | Puri | 166/266 |
| 5,265,678 | 11/1993 | Grundmann | 166/308 |
| 5,332,036 | 7/1994 | Shirley et al. | 166/268 |
| 5,388,640 | 2/1995 | Puri et al. | 166/263 |
| 5,388,641 | 2/1995 | Yee et al. | 166/263 |
| 5,388,642 | 2/1995 | Puri et al. | 166/266 |
| 5,388,643 | 2/1995 | Yee et al. | 166/266 |
| 5,388,645 | 2/1995 | Puri et al. | 166/268 |
| 5,417,286 | 5/1995 | Palmer et al. | 166/308 |
| 5,419,396 | 5/1995 | Palmer et al. | 166/250 |
| 5,439,054 | 8/1995 | Chaback et al. | 166/252 |
| 5,454,666 | 10/1995 | Chaback et al. | 405/52 |
| 5,494,108 | 2/1996 | Palmer et al. | 166/308 |
| 5,501,273 | 3/1996 | Puri | 166/252 |
| 5,513,707 | 5/1996 | Shaw et al. | 166/305.1 X |
| 5,566,755 | 10/1996 | Seidle et al. | 166/263 |
| 5,669,444 | 9/1997 | Riese et al. | 166/263 |
| 5,769,165 | 6/1998 | Bross et al. | 166/266 |
| 5,865,248 | 2/1999 | Riese et al. | 166/263 |

OTHER PUBLICATIONS

Low Temperature Coal Weathering: Its Chemical Nature and Effects on Coal Properties by M.M. Wu, G.A. Robbins, R.A. Winschel & F.P. Burke, Consolidation Coal Company, Library PA 151229 in ENERGY 7 FUELS 1988, 2, 150–157.

Low–temperature oxidation of Victorian brown coal by S. Polat and I.J. Harris, University of Melbourne, Parkville, Victoria 3052 Australia in FUEL, 1984, vol. 63, May, pp.669–672.

Low temperature oxidation of coals, Effects of pore structure and coal composition by Ryuichi Kaji, Yukio Hishinuma and Yoichi Nakamura, Hitachi Research Laboratory, Hitachi Ltd. 4026 Kuji–cho, Hitachi–shi, Ibaraki–ken, 319–12 Japan in FUEL, 1985 vol. 64, Mar., pp. 297–302.

Humic Acids from Coal Controlled Air Oxidation of Coals and Carbons at 150° to 400° by Louis D. Friedman and Corliss R. Kinney, Pennsylvania State College, State College, PA in *Industrial and Engineering Chemistry*, Dec. 1950, vol. 42, No. 12, pp. 2525–2529.

Chlorine Reactions with Organic Substances in *Chlorine Chemistry*, pp. 399–404.

Oxidations of coal by aqueous sodium hypochlorite by Frank R. Mayo and Norman A. Kirshen, SRI International, Menlo Park, CAL in *FUEL* 1979 vol. 58, Oct., pp. 698–704.

Aqueous Alkaline Liquefaction of Southeastern Lignite: Applications to Solution Mining, Recovery of Chemical Feedstocks and Chemical Comminution by Leon Y. Sadler, III and John C. Huang, Unversity of Alabama ©1982 by Marcel Dekker, Inc., pp. 353–375.

Engineering Analysis of in Situ Liquefaction of Coal by D.L. Wise and D.C. Augenstein, Dynatech R/D Company, Cambridge MASS ©1978 by Marcel Dekker, Inc., pp. 173–195.

Conversion of Coal to Simple Compounds by Franklin G. Parker, James P. Fugassi and H.C. Howard, Coal Research Laboratory, Carnegie Institute of Technology, in *Industrial and Engineering Chemistry*, vol. 47, No. 8, pp. 1586–1592.

Chemical Ehancement of Coal Seam Permeability by L.Y. Sader and C. Chang, Unversity of Alabama in *SPE Image Library* 16037.

Ozonization Studies of Coal Constitution by C. R. Kinney and L. D. Friedman, Division of Fuel Technology, Pennsyvania State College, in *Ozonization Studies of Coal Constitution*, vol. 74, Jan. 5, 1952, pp. 57–61.

Chemical Stimulation of Coalbed Methand Wells by Chiehming Chang, Thesis, University, Alabama pp.20–83.

Oxidation of Carbonaceous Materials to Organic Acids by Oxygen at Elevated Pressures by R.C. Smith, R.C. Tomarelli and H. C. Howard, in *The Journal of American Chemical Society*, vol. LXI, Jul.–Dec. 1939 pp. 2398–2402.

The Modeling of Channel Formation During Underground Coal Gasification by B. Dinsmoor, Amoco Chemicals; J.M. Galland, France and T.F. Edgar, SPE–AIME. U. of Texas Austin in *American Institute of Mining, Metallurgical and Petroleum Engineers, Inc., SPE 6185* pp. 1–12.

Chemical Constitution of Coal: As Determined by Oxidation Reactions, by H.C. Howard, Coal Research Laboratory, Carnegie Institute of Technology, Chapter 9 pp. 346–377.

Water–Soluble Polycarboxylic Acids by Oxidation of Coal, by N.W. Franke, N. W. Kiebler, C. H. Ruof, T.R. Savich and H.C. Howard, Coal Research Laboratory, Carnegie Institute of Technology, Pittsburgh, PA, in *Industrial and Engineering Chemistry*, Nov. 1952, pp. 2785–2792.

Feasiblity Study of Coal–Fracture Enhancement Using Aqueous Sodium Hypochlorite, Final Report by A.H. Pelofsky, F.W. Dittman, Rutgers, The State University of New Jersey, Department of Chemical and Biochemical Engineering, Report of Department of Energy, No. DOE/MC/14771–1475.

SPE 20732 Paper entitled: "Enhanced Coalbed Methane Recovery", R. Puri and D. Yee, presented at the 65th Annual Technical Conference and Exhibition of the Sociey of Petroleum Engineers, New Orleans, LA, Sep. 23–26, 1990.

"Multicomponent High–Pressure Adsorption Equilibria on Carbon Substrates: Theory and Data", *Fluid Phase Equilibria*, 78 (1992) pp. 99–137; Elsevier Science Publishers, B.V., Amsterdam.

"Openhole Cavity Completions in Coalbed Methane Wells in the San Juan Basis", I.D. Palmer, Amoco Production Co.: M.J. Mavor, Resource Enterprises, Inc.; J.P. Seidle, J.L. Spitler, and R.F. Volz, Amoco Production Co.

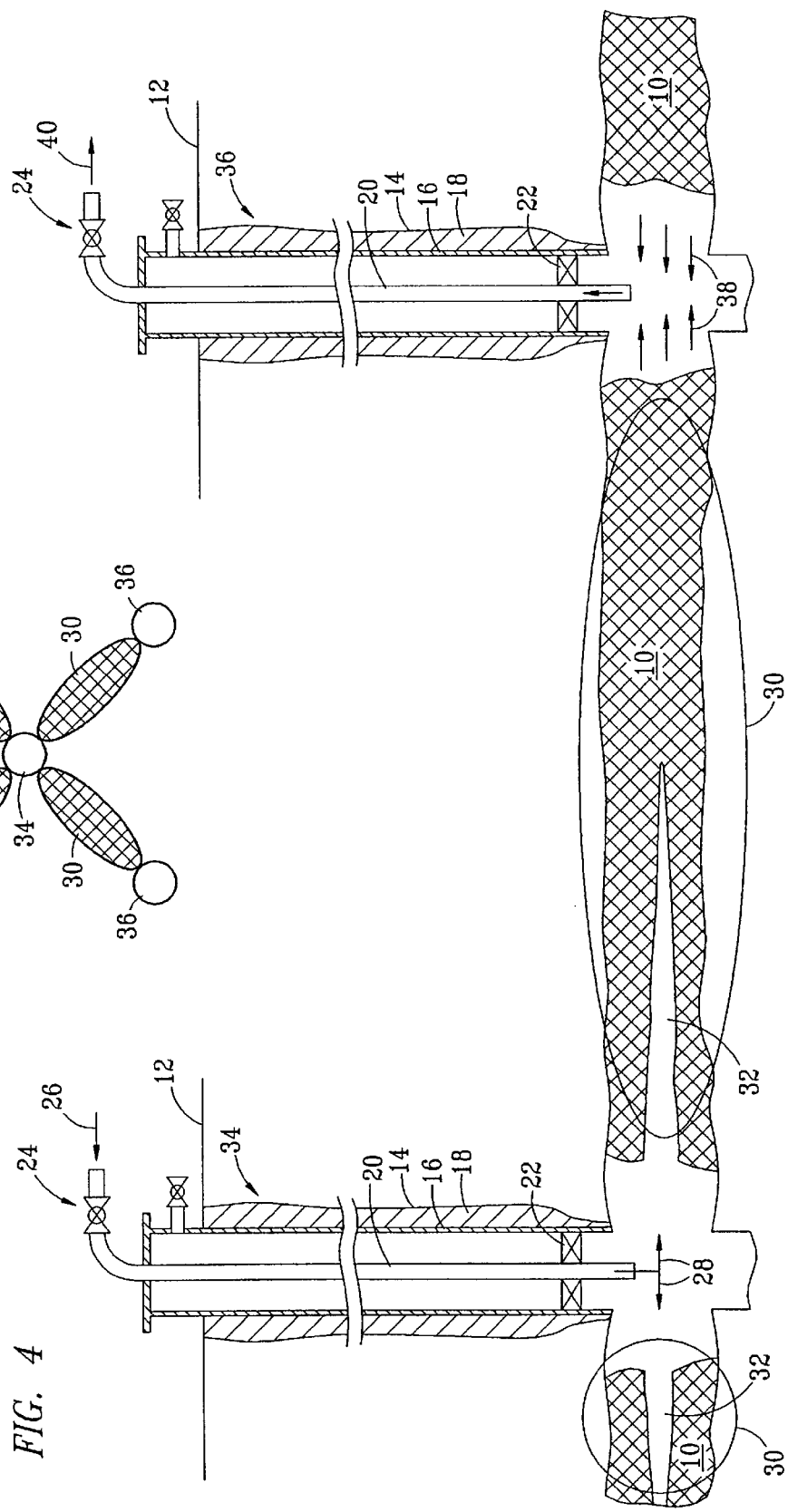

CHEMICALLY INDUCED STIMULATION OF SUBTERRANEAN CARBONACEOUS FORMATIONS WITH GASEOUS OXIDANTS

CROSS-REFERENCE TO RELATED APPLICATION

This application is a continuation-in-part of U.S. Ser. No. 08/846,994, now U.S. Pat. No. 5,865,248, entitled "Chemically Induced Permeability Enhancement of Subterranean Coal Formation" filed Apr. 30, 1997 by Walter C. Riese and Stephen V. Bross which is a continuation-in-part of U.S. Ser. No. 08/594,725, now U.S. Pat. No. 5,669,444, entitled "Chemically Induced Stimulation of Coal Cleat Formation" filed Jan. 31, 1996 by Walter C. Riese and Stephen V. Bross.

BACKGROUND OF THE INVENTION

1. Field of the Invention

This invention relates to methods for increasing the rate of production of methane from a subterranean carbonaceous formation by chemically stimulating the formation with a gaseous oxidant to increase the production rate of methane from the formation. The invention is applicable to the enhanced recovery of methane from formations consisting of carbonaceous materials deposited with inorganic materials, such as occur in carbonaceous shale formations. The increased production rate is accomplished by increasing the surface areas of the contained organic material fragments, which contain hydrocarbons, by inducing the formation of cleats and other new surfaces in these carbonaceous materials, thereby facilitating the desorbtion of light hydrocarbons from these carbonaceous formations. Carbonaceous formations such as shales, are composed in part of clay minerals. The invention is also applicable to the enhanced recovery of light hydrocarbons which are adsorbed to these clay minerals.

2. Brief Description of the Prior Art

Substantial quantities of methane gas are found in subterranean coal formations and in other formations containing carbonaceous materials, which may include macerals, kerogens, and other organic materials and which are present with inorganic materials such as sands, clays and like clastic materials in the formation. Such other formations are referred to herein as "carbonaceous formations".

A variety of processes have been used in attempts to recover the methane from such formations, especially coal formations, more efficiently.

The simplest process is the pressure reduction process wherein a borehole is drilled into a coal formation from the surface and methane is withdrawn from the borehole by reducing the pressure to cause methane to be desorbed from and flow from the coal formation into the borehole and to the surface. This method is not efficient because coal formations are generally not extremely porous and the majority of the methane is generally not found in the pores of the coal formation but is absorbed in or adsorbed to the coal. While methane can be produced from coal formations by this process, the production of methane is relatively slow.

In some coal formations, the natural permeability is sufficient to allow the removal of in situ water to permit the enhanced recovery of methane. In such formations, cleat systems developed during the coal bed diagenesis and burial history provide channel ways through which water and methane migrate to the production wells for removal. This removal of water or "de-watering" of the coal formations removes water from the channel ways and permits the flow of methane through the channel ways and to a production well at a greater rate.

Many coal formations do not have extensively developed cleat systems or have cleat systems which are not fully developed. These coal formations have very low permeability to water and gas and do not yield water or gas at significant rates. As a result, the water fills the cleats, and the recovery of methane from such coal formations is difficult or impossible at significant rates. Such low permeability water-containing coal formations may be either water saturated or less than fully water saturated. It appears that coal formations with better developed cleat systems may have been exposed to a diffusive oxidizing fluid of some type during the geologic past whereas coal formations with less developed cleat systems do not show evidence of past exposure to an oxidizing fluid.

Many formations containing carbonaceous materials in combination with inorganic materials show similar behavior. These are referred to as carbonaceous formations. Many such formations contain large quantities of methane, or other absorbed or adsorbed light hydrocarbons such as methane, but the methane is not readily recovered from such formations because the permeability and exposed surface area of the contained carbonaceous materials are too low to permit the efficient release of methane from the formation.

The terms "absorbed" and "adsorbed" are used interchangeably in the discussion herein to refer to methane or other light hydrocarbons which are retained in or on the surfaces of the carbonaceous materials and the methane or other light hydrocarbons which are retained in or on the surfaces of the clay-mineral materials which are present in the carbonaceous formations.

Accordingly, continuing efforts have been directed to the development of methods for replicating the effects of the conditions which formed the better developed cleat systems in coal formations and increasing the production rate of methane from carbonaceous formations.

SUMMARY OF THE INVENTION

According to the present invention, the rate of recovery of methane from a subterranean carbonaceous formation is increased by positioning at least one well from the surface into the formation; injecting a gaseous oxidant into the formation; maintaining the gaseous oxidant in the carbonaceous formation for a selected time to stimulate the formation of additional surface area or cleats in the organic materials contained in the formation; and producing methane from the formation at an increased rate. The injection of the gaseous oxidant into the formation, and the maintenance of the gaseous oxidant in the formation for a selected period of time stimulates and facilitates the desorbtion of methane and other light hydrocarbons from the carbonaceous materials and the clay-mineral constituents of the formation; allows the methane to migrate from the formation into the wellbore; and allows the methane to be produced from the formation at an increased rate.

Some suitable oxidants are ozone, oxygen, and combinations thereof.

The rate of production of methane from a subterranean carbonaceous formation penetrated by at least one injection well and at least one production well is increased by:

a) Injecting a gaseous oxidant into the formation through the injection well; and b) Producing methane from the formation through the production well at an increased rate.

The present invention is effective to enhance methane recovery from carbonaceous materials disposed with inorganic materials and enhances the recovery of methane from the inorganic materials to which and in which it is adsorbed.

BRIEF DESCRIPTION OF THE DRAWINGS

FIG. 4 is a schematic diagram of an injection well and a production well penetrating a subterranean carbonaceous formation from the surface wherein the carbonaceous formation has been fractured from the injection well.

FIG. 5 is a schematic layout of a 5-spot injection and production well pattern.

DESCRIPTION OF PREFERRED EMBODIMENT

In the discussion of the Figures, the same numbers will be used throughout the specification to refer to the same or similar components.

Figure 1:
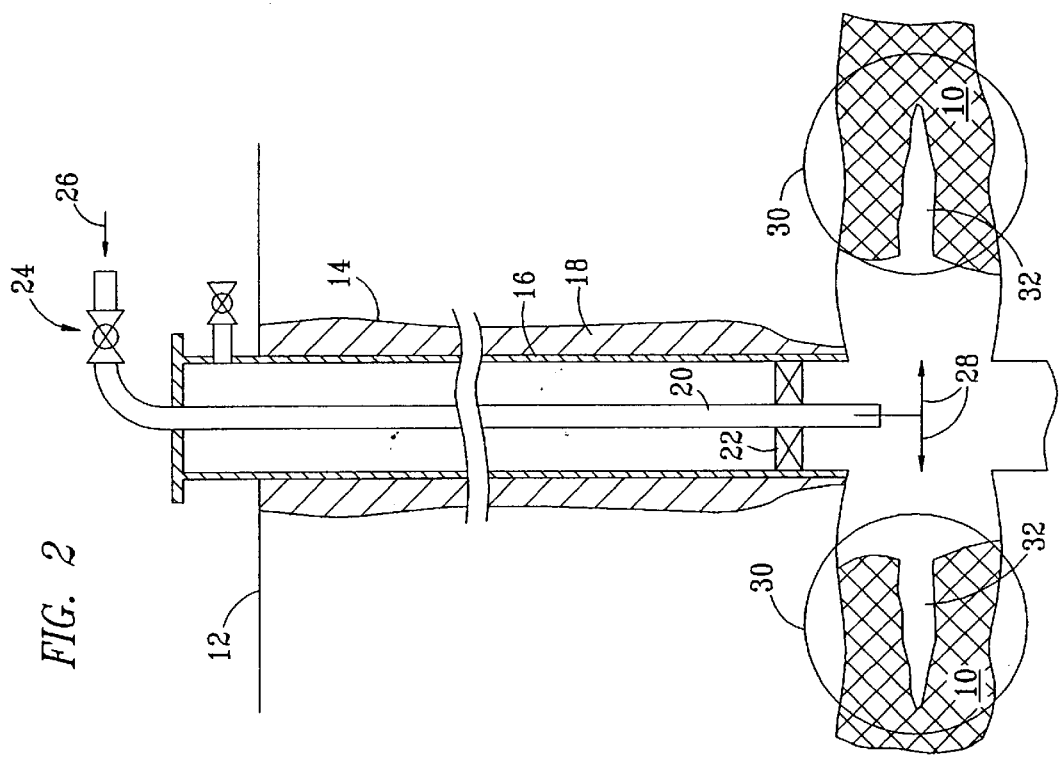
FIG. 1 is a schematic diagram of a well penetrating a subterranean carbonaceous formation from the surface.

In FIG. 1, a carbonaceous formation 10 penetrated from a surface 12 by a wellbore 14 is shown. The wellbore 14 includes a casing 16 positioned in the wellbore 14 by cement 18. While wellbore 14 is shown as a cased wellbore it should be understood that in the preferred embodiments shown in the Figures, cased or uncased wellbores could be used. Alternatively, the casing 16 could be extended into or through carbonaceous formation 10 with perforations through the casing in the carbonaceous formation 10 providing fluid communication between carbonaceous formation 10 and wellbore 14. Wellbore 14 extends into carbonaceous formation 10 and includes a tubing 20 and a packer 22. Packer 22 is positioned to prevent flow between the outer diameter of tubing 20 and the inner diameter of casing 16. Wellbore 14 also includes equipment 24 adapted to inject a gaseous or liquid stream into carbonaceous formation 10 or to recover a gaseous or liquid stream from carbonaceous formation 10.

In the practice of the present invention, a gaseous oxidant is injected as shown by an arrow 26 through tubing 20 into carbonaceous formation 10 as shown by arrows 28. The zones treated are shown by circles 30. The gaseous oxidant is injected into carbonaceous formation 10 for a selected time to enhance or stimulate the formation of additional surface area or cleats in the organic materials contained in carbonaceous formation 10. The gaseous oxidant is injected for a period of time and in a quantity considered sufficient to increase the ability of the organic materials present in carbonaceous formation 10 in the zones 30 to desorb the methane and other light hydrocarbons which are absorbed on and in the organic materials. After a selected period or after a selected amount of the gaseous oxidant has been injected, the well is shut in for a period of time which may be up to or greater than 24 hours. Typically, the well is shut-in until the pressure in the wellbore returns to the formation pressure and thereafter for at least 12 additional hours. Alternatively, a sufficient period of oxidant presence in carbonaceous formation 10 may have elapsed during the injection of the gaseous oxidant. The shut-in period allows for migration of the gaseous oxidant into carbonaceous formation 10 to oxidize components of carbonaceous formation 10; thereby increasing the surface area of, and cleats in, the organic materials present in carbonaceous formation 10. The shut-in period also allows for migration of the oxidant into carbonaceous formation 10 to separate methane and other light hydrocarbons which are adsorbed to the clay-minerals present in carbonaceous formation 10. Subsequent to the shut-in period, water, methane or both may be recovered from carbonaceous formation 10 to de-water carbonaceous formation 10 in the zones 30 and produce methane. The term "de-water" as used herein does not refer to the complete removal of water from carbonaceous formation 10, but rather to the removal of sufficient water from carbonaceous formation 10 to open passage ways in carbonaceous formation 10 so that methane can be produced through the passage ways from carbonaceous formation 10.

The gaseous oxidant contains an oxidant selected from the group consisting of ozone, oxygen, and combinations thereof. Of these, ozone is preferred. When ozone is used the concentrations of ozone in the gaseous oxidant may be up to 100%. Any suitable gaseous diluent may be used if concentrations of ozone below 100% are used.

When oxygen is used the concentrations are suitably up to about 50 percent volume percent of the gaseous oxidant mixture with concentrations up to about 30 volume percent being preferred and with concentrations from about 23 to about 35 volume percent being desirable. The oxygen-containing gaseous oxidant mixture may be air, but is preferably oxygen enriched air containing oxygen at the concentrations stated above. The oxidants can be used in gaseous oxidant mixtures in combination within the ranges discussed above.

Desirably the oxidants are used in gaseous oxidant mixtures which may be adjusted to avoid combustion in the wellbore or coal seam, to avoid gasification or liquification of carbonaceous materials near the wellbore, and the like. Applicants seek to physically modify the structure of the carbonaceous formation to stimulate the formation of cleats and increase the surface area of the carbonaceous materials in the carbonaceous formation in order to increase the permeability of the formation to gas and liquids while avoiding combustion processes. Application of the gaseous oxidant mixture to the carbonaceous formation surfaces, which may be accessed via naturally occurring fractures, artificially created fractures, other existing passageways in the carbonaceous formation and the like, provides access to the carbonaceous materials, which may include coal macerals, to affect the maceral composition, maceral architecture and bonding between maceral faces, thereby stimulating the formation of cleats and a cleat system and increasing the surface area of the carbonaceous materials and increasing the permeability of the carbonaceous formation. This treatment does not result in the removal of solid or particulate carbonaceous material from the carbonaceous formation, or combustion of the carbonaceous material. Rather, the structure of the carbonaceous material is modified; by creation of cleats and cleat systems, thus increasing the surface area and increasing the permeability in the carbonaceous formation to achieve these objectives without removal of solid or particulate carbonaceous material from the formation and without gasification or other physical destruction of the solid material in the carbonaceous formation.

The injection of the gaseous oxidant facilitates the formation of additional free surface area and cleats in the carbonaceous formation and facilitates the release of methane and other light hydrocarbons from the organic materials and from the surfaces of the clay-minerals to which they are adsorbed.

In the embodiment shown in FIG. 1, a single well is used for injection of the gaseous oxidant to chemically enhance or stimulate the formation of additional free surface area and cleats in the organic materials present in carbonaceous formation 10 and facilitate the release of hydrocarbons adsorbed on clay-minerals present in zones 30, to result in the release of formation water and an increase in the methane production rate from carbonaceous formation 10. The term "increase" as used herein refers to a change relative to the untreated carbonaceous formation.

Figure 2:
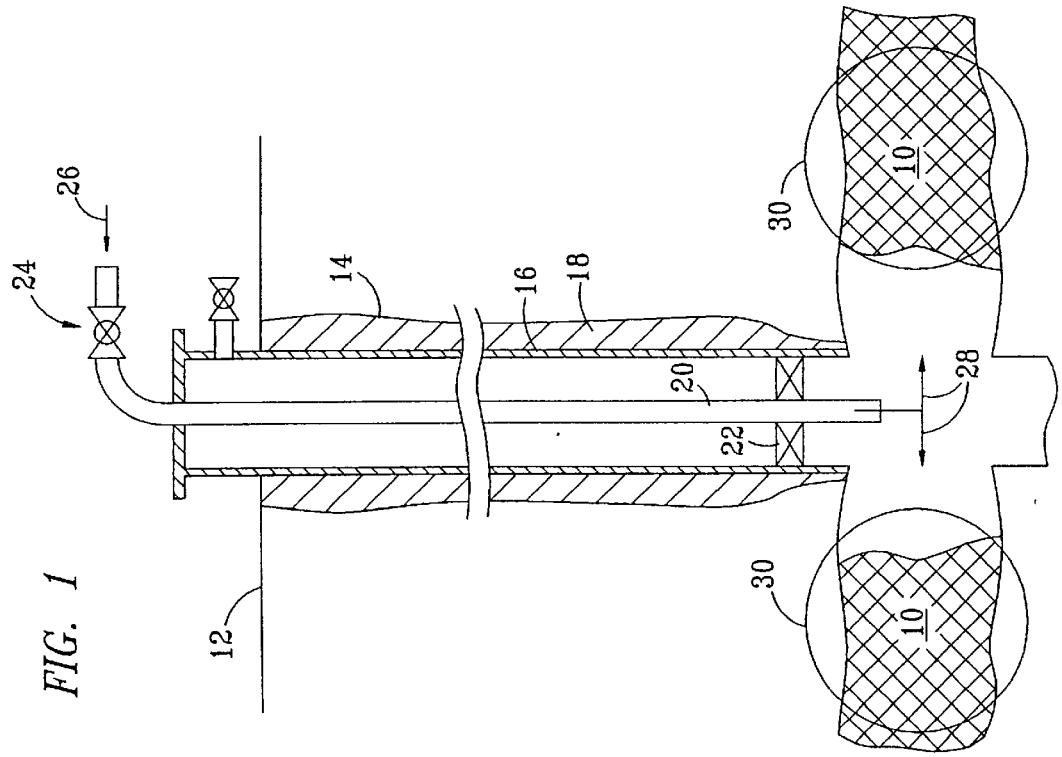
FIG. 2 is a schematic diagram of a well penetrating a subterranean carbonaceous formation from the surface wherein the carbonaceous formation has been fractured.

In FIG. 2, a similar embodiment is shown except that carbonaceous formation 10 has been fractured by fractures 32. The operation of the well is basically the same as that shown in FIG. 1 except that carbonaceous formation 10 has previously been fractured. For instance, it may be desirable to use a conventional fracturing application, if carbonaceous formation 10 is sufficiently impermeable, as an initial stimulation method followed by the gaseous oxidant. In such instances, the well is desirably shut-in as discussed previously and the oxidants are selected from the same oxidant materials discussed previously. The fractures are formed in carbonaceous formation 10 prior to injection of the gaseous oxidant. The gaseous oxidant could be injected above or below the fracture gradient (pressure) if desired.

Figure 3:
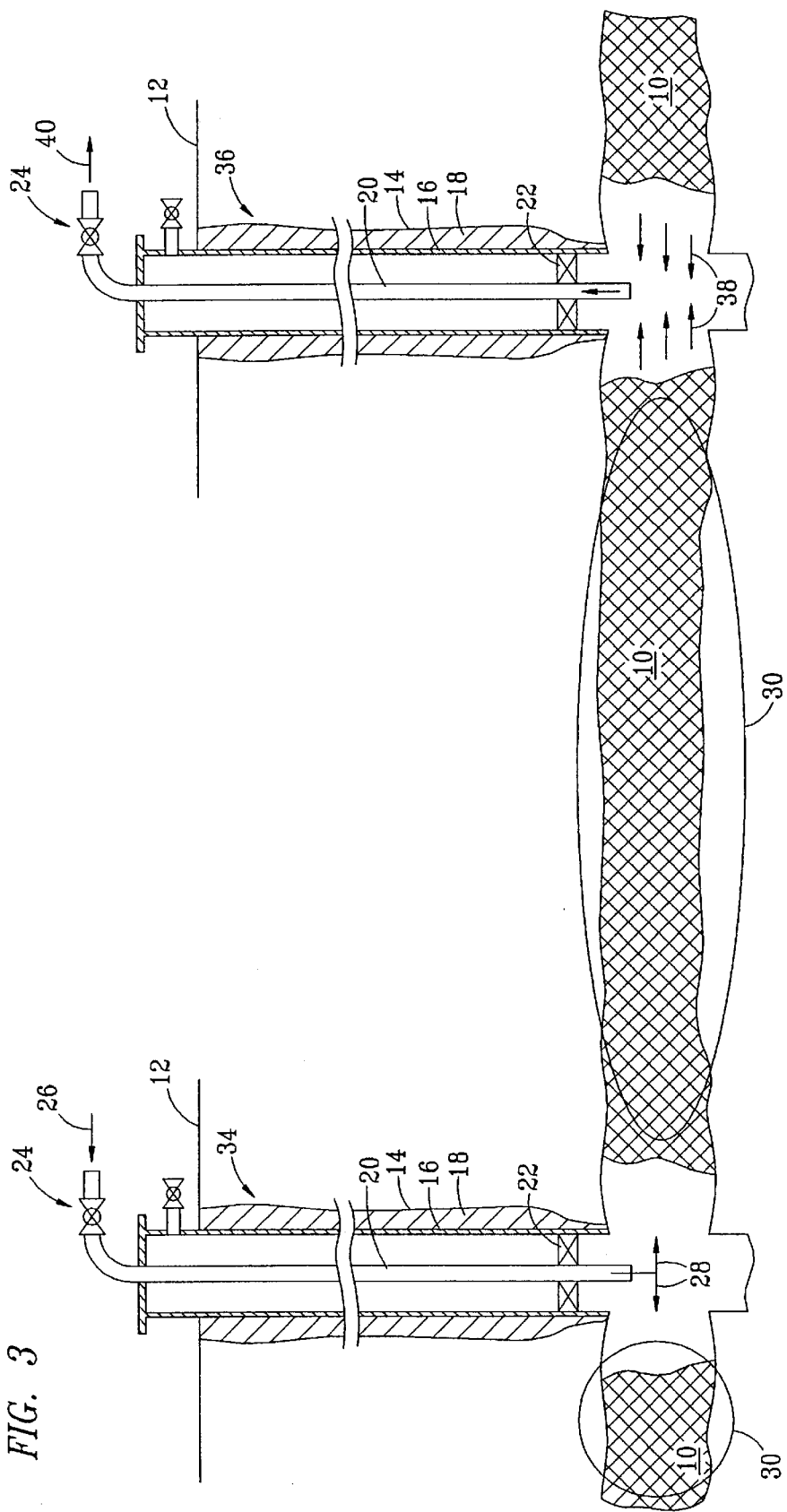
FIG. 3 is a schematic diagram of an injection well and production well penetrating a subterranean carbonaceous formation from the surface.

In FIG. 3, an injection well 34 and a production well 36 penetrate carbonaceous formation 10 from surface 12. Injection well 34 is spaced apart from production well 36 at a spacing based upon the characteristics of the particular carbonaceous formation and the like. According to the present invention, the gaseous oxidant is injected into carbonaceous formation 10 through injection well 34 as shown by arrow 26 and arrows 28 to treat zones 30 which may extend from injection well 34 in a generally circumferential direction, but generally extend preferentially toward a nearby production well or production wells. Production well 36 is positioned to withdraw water and methane from carbonaceous formation 10. The production of water and methane through production well 36 causes the gaseous oxidant to migrate toward production well 36. Desirably, injection of the gaseous oxidant is continued until an increased water volume is detected in production well 36 or until a desired increase in permeability or surface area or an increase in the volume of fluids produced is achieved. The increase in permeability, surface area or volume of fluids produced from production well 36 is indicative of increased permeability, surface area or both in carbonaceous formation 10 and is attended by the release of additional quantities of fluids from carbonaceous formation 10 for production as shown by arrows 38 through production well 36 and by an arrow 40. Arrows 38 are shown directed toward production well 36 from both directions in contemplation that water will continue to be recovered at a lower rate from untreated portions of carbonaceous formation 10.

The embodiment shown in FIG. 4 is similar to that shown in FIG. 3 except that carbonaceous formation 10 has been fractured by fractures 32. Fractures 32 in the embodiment shown in FIG. 2 can be of substantially any extent. By contrast, in the embodiment shown in FIG. 4, fractures 32 desirably extend no more than half way to production well 36. Clearly, if fractures 32 extend completely into production well 36, it will be difficult to use any kind of fluid or gas drive between injection well 34 and production well 36. Desirably, the fractures extend no more than half the distance between injection well 34 and production well 36. The use of the gaseous oxidant with fractures 32 is as discussed previously.

In FIG. 5, a 5-spot well arrangement is shown. Multiple well arrangements, such as 5-spot well arrangements, are useful in the practice of the present invention and may be used in a recurring pattern over a wide area. Such arrangements are well known to those skilled in the art and will be discussed only briefly. In the arrangement shown in FIG. 5, the gaseous oxidant is injected through injection well 34 to treat zones 30 to enhance the recovery of water and methane from the production wells 36. When the desired cleat formation or permeability increase has been achieved as evidenced by the production of fluids at an increased rate from production well 36, the injection of the gaseous oxidant is stopped and injection well 34 can be converted to a production well. The area would then be produced through the original production wells and the converted injection well. The areas of zones 30 which have been treated will yield additional methane production rates and additional ultimate methane recovery.

The method of the present invention is also useful as a pre-treatment for gas injection treatments to enhance the recovery of methane from carbonaceous formation 10. The use of carbon dioxide, either alone or with other gases, to increase the production of methane from coal formations is well known. Similarly, the use of inert gases, such as nitrogen, argon and the like, to remove additional quantities of methane from the coal formations by increasing the pressure in the coal formation and thereby removing additional methane as the methane partial pressure in the atmosphere of the coal seam is decreased is well known to those skilled in the art. The use of such processes requires that the formation be permeable to gas flow into or through the formation so that the methane can be recovered, and also requires that the volumes of methane contained in the organic materials have available free surfaces through which to desorb. The method of the present invention enhances the formation of free surfaces and cleats in the organic materials, and enhances the permeability of the carbonaceous formation where the organic materials are more abundant and forms continuous networks amenable to treatment, and may be used prior to the use of gas sweep or gas desorption treatments to enhance the recovery of methane.

While Applicants do not wish to be bound by any particular theory, the method of the present invention may function by creating free surfaces or a cleat system in the zones of carbonaceous formations contacted by the gaseous oxidant. Generally the method of the present invention is effective to increase the surface area available for the desorption of methane from the macerals, kerogens and other inorganic materials present in the formation which contain quantities of methane. It appears that methane may also be adsorbed to inorganic materials, particularly clays, as well as organic materials in such carbonaceous formations, and that the rate of methane production from both organic and inorganic materials is enhanced by the method of the present invention.

Having thus described the present invention by reference to certain of its preferred embodiments, it is noted that the embodiments discussed are illustrative rather than limiting in nature and that many variations and modifications are possible within the scope of the present invention. Many such variations and modifications may be considered obvious and desirable by those skilled in the art based upon a review of the foregoing description of preferred embodiments.

We claim:

1. A method of increasing the methane recovery from a subterranean carbonaceous formation penetrated by at least one well, the method comprising:

a) injecting a gaseous oxidant into the carbonaceous formation;

b) maintaining at least a portion of the gaseous oxidant in the carbonaceous formation for a selected time to stimulate the formation of cleats in the carbonaceous formation; and c) producing methane from the carbonaceous formation at an increased rate.

2. The method of claim 1 wherein the gaseous oxidant comprises a gaseous oxidant selected from the group consisting of ozone, oxygen and combinations thereof.

3. The method of claim 2 wherein the gaseous oxidant comprises ozone.

4. The method of claim 3 wherein the ozone is diluted with an inert gaseous diluent to form a gaseous oxidant mixture containing up to about 100 volume percent ozone.

5. The method of claim 2 wherein the gaseous oxidant comprises oxygen.

6. The method of claim 5 wherein the oxygen is diluted with an inert gaseous diluent to form a gaseous oxidant mixture containing from about 23 to about 35 volume percent oxygen.

7. The method of claim 5 wherein the gaseous oxidant is air.

8. The method of claim 5 wherein the gaseous oxidant is oxygen-enriched air.

9. The method of claim 8 wherein the oxygen-enriched air contains at least about 30 volume percent oxygen.

10. The method of claim 8 wherein oxygen-enriched air contains at least about 50 volume percent oxygen.

11. The method of claim 1 wherein the gaseous oxidant is injected into the carbonaceous formation through a well; the well is shut-in for a selected time; and thereafter, methane is produced from the well at an increased rate.

12. The method of claim 1 wherein the carbonaceous formation is a formation containing carbonaceous materials which are present with inorganic materials in the formation.

13. A method for increasing the gas permeability of a subterranean carbonaceous formation penetrated by at least one injection well and at least one production well, the method comprising:

a) injecting a gaseous oxidant into the carbonaceous formation through the injection well;

b) maintaining the gaseous oxidant in the carbonaceous formation for a selected time to stimulate the formation of cleats and an increase in the surface area in the carbonaceous materials in the formation; and c) producing methane from the carbonaceous formation through the production well at an increased rate.

14. The method of claim 13 wherein the gaseous oxidant comprises an oxidant selected from the group consisting of ozone, oxygen and combinations thereof.

15. The method of claim 13 wherein the gaseous oxidant comprises ozone.

16. The method of claim 15 wherein the ozone is diluted with an inert gaseous diluent to form a gaseous oxidant mixture containing up to about 100 volume percent ozone.

17. The method of claim 13 wherein the gaseous oxidant comprises oxygen.

18. The method of claim 17 wherein the oxygen is diluted with an inert gaseous diluent to form a gaseous oxidant mixture containing from about 23 to about 35 volume percent oxygen.

19. The method of claim 13 wherein the gaseous oxidant is oxygen-enriched air.

20. The method of claim 13 wherein the carbonaceous formation is a formation containing carbonaceous materials which are present with inorganic materials in the formation.

* * * * *